United States Patent
Eaton

(10) Patent No.: US 9,211,389 B2
(45) Date of Patent: Dec. 15, 2015

(54) OFFSET SOFT TIP WITH PROPOSED TOOLING

(75) Inventor: Elizabeth Eaton, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 443 days.

(21) Appl. No.: 12/957,597

(22) Filed: Dec. 1, 2010

(65) Prior Publication Data

US 2011/0295234 A1  Dec. 1, 2011

Related U.S. Application Data

(60) Provisional application No. 61/267,266, filed on Dec. 7, 2009.

(51) Int. Cl.
*A61M 25/00* (2006.01)

(52) U.S. Cl.
CPC ......... *A61M 25/0068* (2013.01); *A61M 25/001* (2013.01); *A61M 25/008* (2013.01); *A61M 25/0069* (2013.01); *A61M 2025/0059* (2013.01); *A61M 2025/0081* (2013.01)

(58) Field of Classification Search
CPC ..................... A61M 25/0023; A61M 25/0028; A61M 25/003; A61M 25/0032
USPC ........................ 604/548, 96.01, 103.01, 528
See application file for complete search history.

(56) References Cited

U.S. PATENT DOCUMENTS

| | | |
|---|---|---|
| 4,540,404 A | 9/1985 | Wolvek |
| 4,548,206 A | 10/1985 | Osborne |
| 4,619,643 A * | 10/1986 | Bai ................................ 604/43 |
| 4,820,271 A | 4/1989 | Deutsch |
| 4,863,442 A | 9/1989 | DeMello et al. |
| 4,886,506 A | 12/1989 | Lovgren et al. |
| 4,921,483 A | 5/1990 | Wijay et al. |
| 5,078,702 A | 1/1992 | Pomeranz |
| 5,178,158 A | 1/1993 | De Toledo |
| 5,234,416 A | 8/1993 | Macaulay et al. |
| 5,240,537 A | 8/1993 | Bodicky |
| 5,318,032 A | 6/1994 | Lonsbury et al. |
| 5,366,442 A | 11/1994 | Wang et al. |
| 5,531,700 A * | 7/1996 | Moore et al. ............. 604/164.13 |
| 5,545,149 A | 8/1996 | Brin et al. |
| 5,676,659 A | 10/1997 | McGurk |
| 5,769,830 A | 6/1998 | Parker |
| 5,860,963 A | 1/1999 | Azam et al. |

(Continued)

FOREIGN PATENT DOCUMENTS

EP  1 980 289 A2  10/2008

OTHER PUBLICATIONS

McLellan, Garey L.; A New Percutaneous Access Set for Interventional Procedures; AJR/Technical Note; 1991; 156:397-399; American Roentgen Ray Society.

*Primary Examiner* — Edelmira Bosques
(74) *Attorney, Agent, or Firm* — Brinks Gilson & Lione

(57) ABSTRACT

A medical catheter device is disclosed that comprises a tubular shaft member, a soft tip member, and a wire guide lumen extending longitudinally within the tubular shaft member and the soft tip member. The wire guide lumen is offset relative to the centerline within the soft tip member. By offsetting the inner diameter of the soft tip member in such a way as to not change the outward profile of the catheter, the soft tip will have improved tracking across existing stents and eccentric lesions.

6 Claims, 2 Drawing Sheets

(56) References Cited

U.S. PATENT DOCUMENTS

| | | |
|---|---|---|
| 5,938,653 A | 8/1999 | Pepin |
| 6,135,992 A | 10/2000 | Wang |
| 6,245,053 B1 | 6/2001 | Benjamin |
| 6,761,703 B2 | 7/2004 | Miller et al. |
| 6,814,744 B2 | 11/2004 | Yang et al. |
| 6,869,414 B2 | 3/2005 | Simpson et al. |
| 2005/0059959 A1 | 3/2005 | Eidenschink |

* cited by examiner

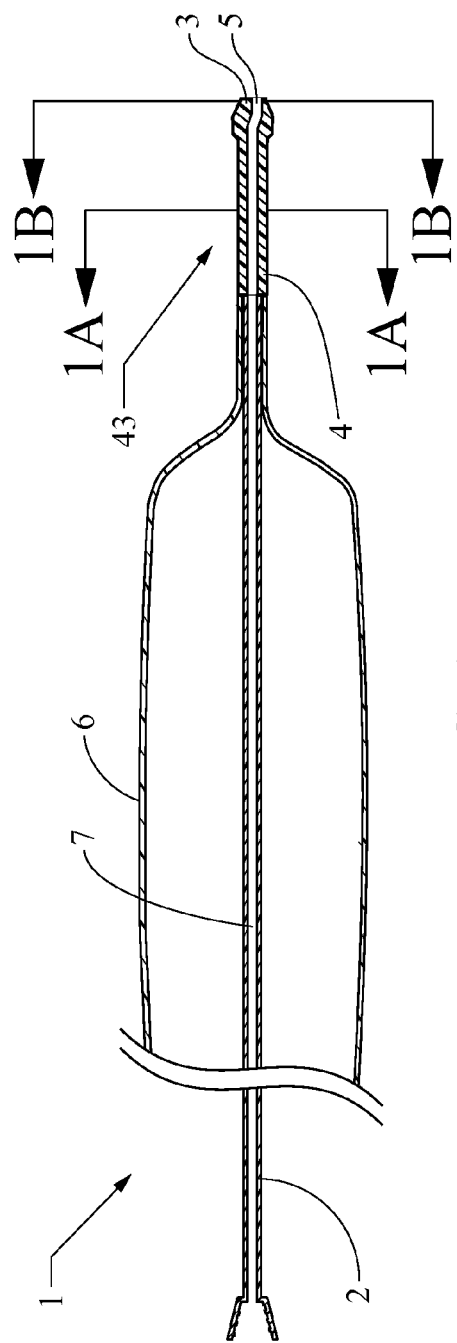

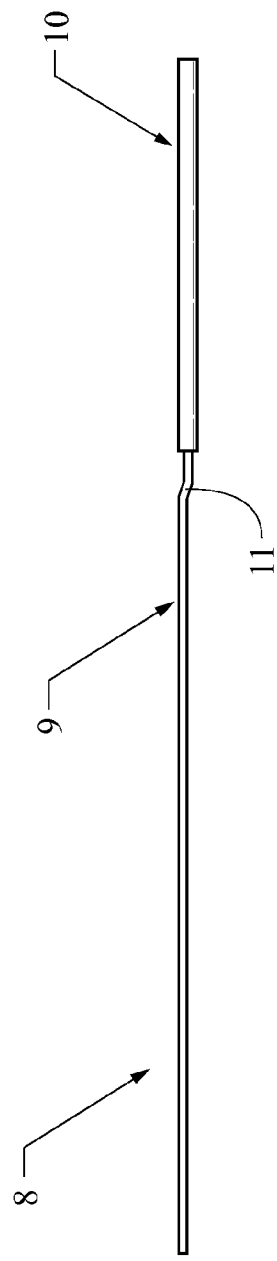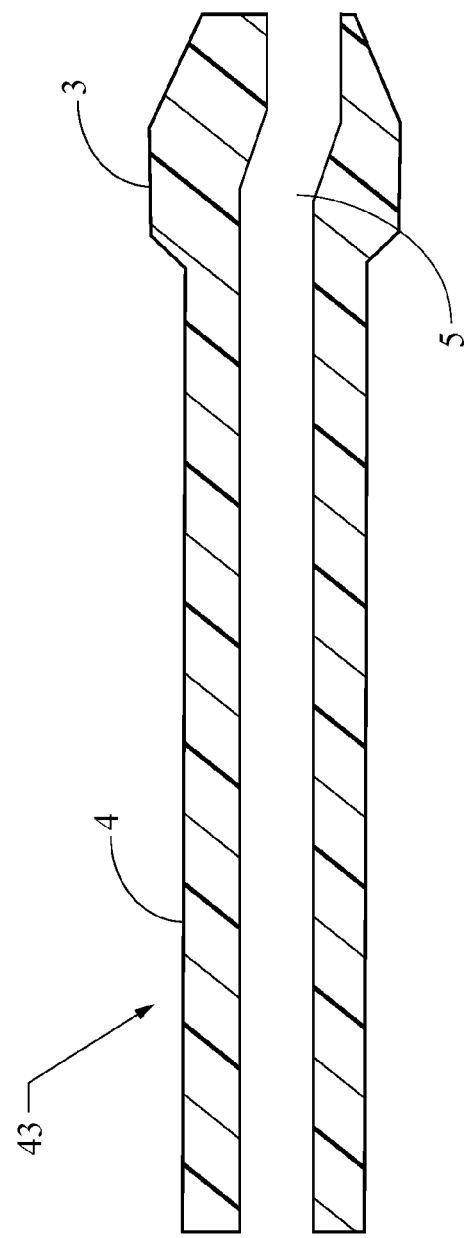
FIG. 2
FIG. 3

OFFSET SOFT TIP WITH PROPOSED TOOLING

RELATED APPLICATION

The present application claims the benefit of U.S. Provisional Application No. 61/267,266, filed on Dec. 7, 2009, the entirety of which is hereby incorporated by reference.

BACKGROUND

Catheters are tube-like medical devices that are inserted into a body organ or blood vessel for diagnostic or therapeutic reasons. One of the therapeutic procedures applicable to the present invention is known as percutaneous translumenal angioplasty (PTA). During such a procedure, a catheter may be inserted through the skin and traverse long distances through vessels. The more fragile or tortuous tissue of these structures may be easily irritated, perforated, or otherwise damaged by the catheter tip. Furthermore, a catheter may be required to cross an already-stented vessel segment. Particularly in small vessels, the danger exists that the catheter may become entangled with the existing implant struts. This may result in damage to the stent, damage to the surrounding tissue, or damage to the catheter.

Catheters must have sufficient stiffness to be pushed long distances through vessels as well as sufficient rigidity to provide torsional control. However, stiffness or rigidity in the catheter tip poses the danger of puncturing or otherwise damaging a vessel as it twists through the vascular system as discussed above. This problem has been addressed in the past by forming the distal end of the relatively rigid catheter with a relatively soft tip which is either atraumatic or significantly less traumatic to vessel wall tissue than the more rigid material forming the body of the catheter. Examples of such soft tip catheters are known in the art.

To move a catheter through the vascular system more easily, the ends of the soft tips are often tapered. The tapering provides a gradual change in diameter along the length, while the material transition provides a change in durometer between the soft tip and the main tubular portion of the catheter. However, the tapered end has limited benefits when approaching a stented sharp turn, such as a renal ostium with in-stent restenosis being approached via the aorta. The symmetric nature of the tapered end does not provide any specific directional benefit. The present invention provides an improvement towards the resolution of this problem.

BRIEF SUMMARY

The present invention is directed to a catheter having a distal soft tip with an offset inner diameter. By creating a non-symmetric cross section at the soft tip, the tip can be more easily tracked across existing stents and eccentric lesions.

Currently soft-tip bonding is done with a step mandrel. Two different diameters of mandrel are abutted to each other. Typically, the portion of the mandrel having the smaller diameter is used to form the catheter tip and the portion of the mandrel having the larger diameter is used to hold and secure the mandrel during the manufacturing process and form the distal end of the catheter tip. In this invention the section of the mandrel that defines a smaller diameter includes a curve just proximal to the section of the mandrel that defines a larger diameter. The proximal portion of the mandrel that defines a smaller diameter is inserted through the soft tip lumen into the proximal end of the tip such that the curve is located within the soft distal end of the tip. Next, a segment of shrink tubing may be slid longitudinally over the mandrel, the proximal end of the tip, and the soft distal end of the tip. Heat is applied. The heat causes the proximal end of the tip and the soft distal end of the tip to become flowable while the heat shrink contracts radially, thereby bonding both segments. By adding a curve to the smaller diameter mandrel end just proximal to the step, a consistent curve within the distal soft tip will be achieved during the bonding process such that the lumen of the soft tip will be continuous with but slightly offset from the remainder of the catheter wire guide lumen. The wall of the soft tip material will become thicker on one side than the other, providing a directional difference in the flexibility of the tube.

BRIEF DESCRIPTION OF THE DRAWINGS

FIG. 1 is a cross-sectional view of the catheter with an offset soft tip.

FIG. 1A is a transverse cross-sectional view of the symmetric section of the soft tip.

FIG. 1B is a transverse cross-sectional view of the asymmetric section of the soft tip.

FIG. 2 is a step mandrel with a curve.

FIG. 3 is an enlarged cross-sectional view of the distal soft tip.

DETAILED DESCRIPTION OF THE DRAWINGS AND THE PRESENTLY PREFERRED EMBODIMENTS

For the purposes of promoting and understanding the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art.

Referring now to the drawings, as illustrated in FIG. 1, catheter 1 comprises a tubular shaft member 2, a balloon 6, a distal tip member 43 having a distal tip section 3 and a proximal tip section 4, an inner wire guide lumen 7, and a soft tip lumen 5.

The diameter of the wire guide lumen 7 will vary depending upon the requirements of the catheter 1 to be placed in the body, which are themselves dependent upon the size of the blood vessel or vessels to be catheterized, as well as distance to the lesion and a variety of other factors.

The distal tip member 43 constitutes the most distal end of the catheter 1 and the distal tip section 3 constitutes the most distal end of the distal tip member 43. The distal tip section 3 is made of a softer material relative to the material of the proximal tip section 4 and the tubular shaft member 2 to provide enhanced trackability and minimize trauma to the inner surface of a blood vessel through which the catheter 1 may pass. In addition, it must be hard enough to maintain an opening therethrough to allow the passage of a wire guide or other interventional medical device to pass out of the tubular shaft member 2 and the proximal tip section 4 and through the distal tip section 3. The soft material may comprise, for example, a polyether block amide such as nylon. The distal tip section 3 is tapered to ensure a gradual transition from the proximal end of the distal tip section 3 to the distal end of the distal tip section 3. A grinding process or other suitable tipping process may be used to reduce the exterior diameter of the distal tip section 3 as appropriate for the desired application.

The distal tip section 3 is tubular and has a side wall that surrounds the soft tip lumen 5, which is continuous with the wire guide lumen 7 of the tubular shaft member 2. The distal tip section 3 has a non-symmetric cross section such that the distal section of the soft tip lumen 5 is offset relative to the center line of the wire guide lumen 7 as seen in FIG. 1. FIG. 1A is a transverse cross section along line 1A-1A of FIG. 1, and shows the symmetric section of the wall of the proximal end of the distal tip section 3. FIG. 1B is a transverse cross section along line 1B-1B of FIG. 1, and shows the asymmetric section of the distal tip section 3. FIG. 3 is an enlarged cross-sectional view of the distal tip member 43 showing the offset inner diameter of the distal tip section 3. By offsetting the inner diameter of the distal tip section 3 in such a way as to either change or not change the outward profile of the catheter 1 but to still affect the relative stiffness on either side of a wire guide passing through the catheter 1, directional advantage is achieved, facilitating the tracking of the catheter tip 43 through blood vessels. Because of the asymmetric cross-section of the distal tip section 3, one side of the distal tip section 3 will be more flexible than the opposite side relative to the soft tip lumen 5, such that the distal tip section 3 will tend to curve towards the side of greater flexibility along a curved wire guide. The curve in the wire guide may be built into the wire guide or may be created by the anatomy. Either with or in the absence of a wire guide, the asymmetrically centered soft tip lumen 5 of the distal tip section 3 will cause the catheter tip 43 to more easily divert away from obstructions (such as stents or even plaques, in cases of chronic total occlusions where false lumen passage is desirable). Additionally, a curve induced in the distal tip section 3, will retain its shape for a longer period of time due to the bias of the proximal tip section 4 to curve in that particular direction.

The distal tip section 3 is preferably pre-formed having an inner lumen, side wall thickness, and an outer diameter, the diameter of the inner lumen closely matching the diameter of the lumen of the proximal tip section 4 at the interface of the distal tip section 3 and proximal tip section 4 so as to provide a lumen having a constant diameter. As best seen in FIG. 3, the outer diameter of the proximal tip section 4 is smaller than the outer diameter of the distal tip section 3 to accommodate attachment of the neck of the balloon there about (not shown) and provide a constant outer diameter.

As illustrated in FIG. 2, the step mandrel 8 is composed of a proximal mandrel section 9 and a distal mandrel section 10. The diameter of the proximal mandrel section 9 is smaller relative to the diameter of the distal mandrel section 10. The proximal mandrel section 9 further comprises a bend or a curve 11 just proximal to the distal mandrel section 10.

The offset profile of the distal tip section 3 is achieved during the step mandrel bonding of the proximal tip section 4 and the distal tip section 3. Step mandrel bonding is known in the prior art. To bond the distal tip section 3 to the distal end of the proximal tip section 4, the proximal mandrel section 9 of the step mandrel 8 is inserted into the distal tip section 3 such that the curve 11 of the step mandrel 8 is inside the soft tip lumen 5 of the distal tip section 3. The distal mandrel section 10 extends outwardly from the distal end of the distal tip section 3. Next, the proximal tip section 4 is advanced over the proximal mandrel section 9. The diameter of the step mandrel 8 may approximate or be smaller than the inner diameter of the proximal tip section 4.

Next, a segment of heat shrink tubing may be advanced over the step mandrel 8, the proximal tip section 4, and the distal tip section 3 and centered longitudinally over the junction of the proximal tip section 4 and the distal tip section 3. The heat shrink tubing may be of TEFLON® polytetrafluoroethylene (PTFE) or any other material used in the prior art. Heat is applied at the interface of the distal tip section 3 and the proximal tip section 4, such that the materials may flow together. Means of heating include, for example, forced convective heating, radio frequency heating, ultrasonic welding, and laser bonding. The heat shrink tubing may be removed or may remain on as part of the connected structure. Alternatively, the heat shrink tubing may be omitted and heat may be applied directly at the junction of the distal tip section 3 and the proximal tip section 4.

Once the heating cycle is complete and cooling accomplished, the step mandrel 8 is removed from the inside of the bonded assembly. The distal tip section 3 of the distal tip member 43 of the catheter 1 will now have an offset inner diameter.

The bonding of the balloon 6 to the distal tip member 43 can take place before, during, or after the mandrel bonding of the proximal tip section 4 and the distal tip section 3.

A balloon catheter assembly is well known in the art. The catheter assembly may consist of a balloon 6, a tubular shaft member 2, and a distal tip member 43, wherein the tubular shaft member 2 is attached to a proximal tip section 4 which is attached to a distal tip section 3 of the distal tip member 43. The catheter assembly may further include a PTFE introducer sheath for percutaneous introduction of the catheter assembly into a body vessel. The introducer sheath receives and provides stability to the catheter assembly at a desired location of the body vessel. A wire guide may be provided to be percutaneously inserted within the vasculature to guide the catheter assembly to the desired location (Seldinger technique). The catheter assembly may also include a handle provided with a lumen through which the wire guide and/or the catheter 1 can slide.

The preceding specific embodiments are illustrative of the practice of the preferred embodiment. It is to be understood, however, that other expedients known to those skilled in the art or disclosed herein may be employed without departing from the spirit of the invention or the scope of the appended claims.

The invention claimed is:

1. A medical catheter, comprising:
    a tubular shaft member having a proximal shaft end, a distal shaft end, and a shaft outer diameter enclosing a wire guide lumen, at least a distal portion of the wire guide lumen extending longitudinally within the tubular shaft member along a central longitudinal axis of the tubular shaft member; and
    a distal tip member having a proximal end and a distal end, the proximal end being continuous with the distal shaft end, the distal tip member defining a distal tip lumen in communication with the wire guide lumen, the distal tip lumen extending between the proximal end and a distal end opening disposed on the distal end of the distal tip and having a constant cross-section along the length thereof,
    wherein the distal tip lumen comprises a proximal tip lumen section and distal tip lumen section, the proximal tip lumen section being disposed about a proximal tip lumen section axis that is aligned with and coincident with the central longitudinal axis of the tubular shaft member, the distal tip lumen section and the distal end opening both being disposed about a distal tip lumen section axis that is offset relative to the central longitudinal axis of the tubular shaft member, the distal tip lumen section axis being parallel to the central longitudinal axis of the tubular shaft member and wherein the distal tip member comprises a proximal tip section and a distal tip section, the proximal tip section having a symmetrical cross-sectional area having a circular outer diameter radially disposed about the proximal tip lumen section axis, and the distal tip section having an asymmetrical cross-sectional area having a circular outer diameter radially offset from the distal tip lumen section axis.

2. The catheter of claim 1 wherein the distal tip lumen comprises a constant diameter that is substantially equal to a diameter of the wire guide lumen.

3. The catheter of claim 1 wherein the distal tip section comprises a softer material relative to a material of the proximal tip section.

4. The catheter of claim 1 wherein an outer surface of the distal tip section is tapered inwardly towards the distal end of the tip.

5. The catheter of claim 1 wherein the distal tip lumen further comprises an intermediate tip lumen section disposed between and in communication with the proximal tip lumen section and the distal tip lumen section, the intermediate tip lumen section extending along an axis that is angled relative to the central axis of the tubular shaft section.

6. The catheter of claim 5 wherein the proximal tip lumen section, the intermediate tip lumen section, and the distal tip lumen section extend generally along an S-shaped pathway.

* * * * *